(12) United States Patent
Taylor et al.

(10) Patent No.: US 11,992,412 B2
(45) Date of Patent: May 28, 2024

(54) RADIAL HEAD FRACTURE TREATMENT SYSTEM

(71) Applicant: In2Bones USA, LLC, Memphis, TN (US)

(72) Inventors: Alan G. Taylor, Memphis, TN (US); Rebecca Hawkins Wahl, Escondido, CA (US)

(73) Assignee: In2Bones USA, LLC, Memphis, TN (US)

(*) Notice: Subject to any disclaimer, the term of this patent is extended or adjusted under 35 U.S.C. 154(b) by 539 days.

(21) Appl. No.: 17/198,075

(22) Filed: Mar. 10, 2021

(65) Prior Publication Data
US 2021/0290401 A1    Sep. 23, 2021

Related U.S. Application Data

(60) Provisional application No. 62/991,427, filed on Mar. 18, 2020.

(51) Int. Cl.
| A61F 2/46 | (2006.01) |
| A61B 17/92 | (2006.01) |
| A61F 2/38 | (2006.01) |
| A61F 2/30 | (2006.01) |

(52) U.S. Cl.
CPC ............ *A61F 2/3804* (2013.01); *A61B 17/92* (2013.01); *A61F 2/4605* (2013.01); *A61F 2/4684* (2013.01); *A61B 2017/922* (2013.01); *A61F 2002/30607* (2013.01); *A61F 2002/3827* (2013.01)

(58) Field of Classification Search
CPC .... A61F 2/4606; A61F 2/4684; A61F 2/3804; A61F 2/4605; A61F 2002/4659; A61F 2/4607; A61F 2/4612; A61F 2/4618; A61F 2002/4628; A61B 17/92–2017/924
See application file for complete search history.

(56) References Cited

U.S. PATENT DOCUMENTS

| 5,251,642 A | * | 10/1993 | Handlos | ................. | A61B 90/06 600/587 |
| 6,270,529 B1 | * | 8/2001 | Terrill-Grisoni | ...... | A61F 2/3804 623/20.11 |
| 6,709,459 B1 | * | 3/2004 | Cooney, III | .......... | A61F 2/3804 623/20.11 |

(Continued)

*Primary Examiner* — Alvin J Stewart
(74) *Attorney, Agent, or Firm* — Rutan & Tucker LLP; Hani Z. Sayed

(57) ABSTRACT

A system and methods are provided for treating radial head fractures. The system includes an implant, a sterile instrument kit for radial head arthroplasty, and a head sizer and assembly tray for sizing and assembling implants. The implant includes a head that is coupled with a stem. The head is adapted to be placed into sliding contact with a capitellum of the radiocapitellar joint. The stem is configured to be inserted into a hole reamed into a medullary canal of the radial head. The sterile instrument kit comprises a multiplicity of instruments including any one or more of trial heads and trial stems, a starter awl, a reamer, a planar, an inserter cap, and an impactor. The instruments are configured for implanting the implant into the radiocapitellar joint such that the implant restores biomechanical properties of the joint.

21 Claims, 4 Drawing Sheets

(56) References Cited

U.S. PATENT DOCUMENTS

| | | | |
|---|---|---|---|
| 7,845,077 B1* | 12/2010 | Alulis | A44C 9/02 264/296 |
| 2001/0037154 A1* | 11/2001 | Martin | A61F 2/4637 623/20.12 |
| 2005/0075735 A1* | 4/2005 | Berelsman | A61F 2/3804 623/908 |
| 2006/0052725 A1* | 3/2006 | Santilli | A61B 5/107 623/20.11 |
| 2006/0116771 A1* | 6/2006 | Cooney | A61F 2/3804 623/20.11 |
| 2006/0142866 A1* | 6/2006 | Baratz | A61F 2/3804 623/23.45 |
| 2006/0282169 A1* | 12/2006 | Felt | A61F 2/3804 623/20.11 |
| 2009/0240336 A1* | 9/2009 | Vander Meulen | A61F 2/3804 623/18.11 |
| 2011/0035016 A1* | 2/2011 | Orbay | A61F 2/3804 623/20.11 |
| 2012/0083892 A1* | 4/2012 | Kehres | A61F 2/3804 623/20.11 |
| 2013/0018382 A1* | 1/2013 | Jones | A61F 2/4603 623/20.35 |
| 2014/0012388 A1* | 1/2014 | Brownhill | A61F 2/3804 623/20.13 |
| 2014/0074246 A1* | 3/2014 | Huebner | A61F 2/3804 623/20.11 |
| 2014/0277524 A1* | 9/2014 | Brownhill | A61F 2/3804 623/20.11 |
| 2015/0335437 A1* | 11/2015 | Bruun Lauritzen | A61F 2/34 623/23.12 |
| 2015/0366677 A1* | 12/2015 | Porzel | A61L 27/50 623/20.35 |
| 2016/0066973 A1* | 3/2016 | Borries | A61B 17/92 606/100 |
| 2016/0175115 A1* | 6/2016 | Baratz | A61F 2/4657 606/102 |
| 2017/0095338 A1* | 4/2017 | Bergquist | A61F 2/3804 |
| 2017/0156739 A1* | 6/2017 | Nino | B25D 5/02 |
| 2017/0224434 A1* | 8/2017 | Schwartzbauer | A61B 50/33 |
| 2018/0214233 A1* | 8/2018 | Termanini | A61F 2/3609 |
| 2018/0221171 A1* | 8/2018 | Termanini | A61F 2/4609 |
| 2018/0280148 A1* | 10/2018 | Winslow | A61F 2/4612 |
| 2019/0254829 A1* | 8/2019 | Hodorek | A61F 2/3804 |
| 2019/0298530 A1* | 10/2019 | Hodorek | A61F 2/3804 |
| 2019/0314159 A1* | 10/2019 | Klinger | A61F 2/30749 |
| 2019/0358042 A1* | 11/2019 | Taylor | A61F 2/4225 |
| 2020/0046448 A1* | 2/2020 | Hodorek | A61B 90/06 |
| 2020/0046505 A1* | 2/2020 | Forsell | A61F 2/32 |
| 2020/0078178 A1* | 3/2020 | Carter | A61F 2/30756 |
| 2020/0253740 A1* | 8/2020 | Puncreobutr | A61B 17/15 |
| 2021/0100660 A1* | 4/2021 | Lequette | A61F 2/4684 |
| 2021/0121296 A1* | 4/2021 | Schreiber | A61B 17/15 |
| 2022/0071644 A1* | 3/2022 | Donner | A61B 17/144 |
| 2022/0202592 A1* | 6/2022 | Clarke | A61F 2/4606 |
| 2022/0249239 A1* | 8/2022 | Williams | A61B 17/1764 |
| 2022/0330995 A1* | 10/2022 | Gililland | A61B 17/1675 |
| 2022/0346975 A1* | 11/2022 | Mattson | A61F 2/4657 |
| 2022/0395375 A1* | 12/2022 | Stowell | A61F 2/4601 |

* cited by examiner

RADIAL HEAD FRACTURE TREATMENT SYSTEM

PRIORITY

This application claims the benefit of and priority to U.S. Provisional Application, entitled "Radial Head Fracture Treatment System," filed on Mar. 18, 2020 and having application Ser. No. 62/991,427, the entirety of said application being incorporated herein by reference.

FIELD

Embodiments of the present disclosure generally relate to the field of surgical implants. More specifically, embodiments of the disclosure relate to a system and methods for treating radial head fractures that restore the biomechanical properties of the native radial head when radial head arthroplasty is performed.

BACKGROUND

Indications for surgical management of radial head fractures are well defined in the literature. Fragment size, number, degree of displacement, and bone quality influence decision making regarding optimal management. Associated injuries and a block to motion are also important factors to consider. Good results have been reported after open resection and internal fixation (ORIF) for selected non-comminuted displaced radial head fractures. Radial head fragment excision and early or delayed radial head excision all have a role in the management of these common injuries. Radial head fractures that are displaced but are too comminuted to be anatomically reduced and stably fixed with ORIF and which are too large to consider fragment excision (fracture involves greater than ¼ of the radial head), should be managed by radial head excision or arthroplasty. Patients known to have or likely to have an associated ligamentous injury of the elbow or forearm should undergo a radial head arthroplasty because radial head excision is contraindicated.

Considering that radial head fractures are one of the most common bone injuries to the adult elbow, there is a continuous desire to develop treatments for elbow injuries that improve patient care. Embodiments presented herein provide a system and methods for treating radial head fractures that restore the biomechanical properties of the native radial head when radial head arthroplasty is indicated.

SUMMARY

A system and methods are provided for treating radial head fractures. The system includes an implant, a sterile instrument kit for radial head arthroplasty, and a head sizer and assembly tray for sizing and assembling implants. The implant includes a head that is coupled with a stem. The head is adapted to be placed into sliding contact with a capitellum of the radiocapitellar joint. The stem is configured to be inserted into a hole reamed into a medullary canal of the radial head. The sterile instrument kit comprises a multiplicity of instruments including any one or more of trial heads and trial stems, a starter awl, a reamer, a planar, an inserter cap, and an impactor. The instruments are configured for implanting the implant into the radiocapitellar joint such that the implant restores biomechanical properties of the joint.

In an exemplary embodiment, a system for treating radial head fractures comprises: one or more implants configured for radial head arthroplasty; a sterile instrument kit comprising a multiplicity of instruments including any one or more of trial heads and trial stems, a starter awl, a reamer, a planar, an inserter cap, and an impactor, the multiplicity of instruments being configured for implanting the one or more implants into a patient's body such that the implant restores biomechanical properties of the native radial head; and a head sizer and assembly tray configured to correspond to sizes of the one or more implants.

In another exemplary embodiment, the one or more implants each includes a head that is coupled with a stem. In another exemplary embodiment, the head is a cylindrical member comprising: a rounded periphery comprising a smooth surface configured to contact bone and tissues surrounding a radiocapitellar joint without causing damage or trauma to the bone and tissues; a contact surface adapted to be placed into sliding contact with a capitellum comprising the radiocapitellar joint; and a tapered bore configured to fixedly receive a tapered shank comprising the stem. In another exemplary embodiment, the stem is an elongate member configured to be inserted into a hole reamed into a medullary canal of a radial head and comprises: a tapered shank configured to be fixated within a tapered bore of the head; and a tapered tip configured to facilitate inserting the stem into the hole.

In another exemplary embodiment, the starter awl comprises a proximal handle coupled with a shaft that terminates at a distal tip and is configured for creating an opening in a radial head medullary canal during a radial head arthroplasty. In another exemplary embodiment, the proximal handle comprises a biocompatible plastic that is injection molded onto the shaft during manufacturing the starter awl. In another exemplary embodiment, the reamer comprises a proximal handle coupled with a shaft that terminates at a distal cutting teeth area and is configured to be used to form a hole in a radial head medullary canal during a radial head arthroplasty. In another exemplary embodiment, the proximal handle comprises a biocompatible plastic that is injection molded onto the shaft during manufacturing the reamer.

In another exemplary embodiment, the planar comprises a proximal handle coupled with a shaft that includes planar cutting teeth and a distal stem, the planar being configured to facilitate forming a smooth contact surface on a radial neck during a radial head arthroplasty. In another exemplary embodiment, the proximal handle is configured to be grasped in a hand during inserting the distal stem into a radial head medullary hole and during twisting the planar to cut the smooth contact surface into the radial neck. In another exemplary embodiment, the proximal handle comprises a biocompatible plastic that is injection molded onto the shaft during manufacturing the planar.

In another exemplary embodiment, the inserter cap is configured to be coupled with the planar for pushing any one of the one or more implants into a radial head medullary hole during a radial head arthroplasty. In another exemplary embodiment, the inserter cap comprises a central hole and a smooth distal surface. In another exemplary embodiment, the central hole is adapted to receive a distal stem comprising a planar such that the inserter cap is removably fixated onto the planar. In another exemplary embodiment, the distal surface is configured to be pressed against the any one of the one or more implants.

In another exemplary embodiment, the head sizer and assembly tray is configured to facilitate determining a suitable diameter of a head comprising the one or more implants to be implanted during a radial head arthroplasty. In another exemplary embodiment, the tray comprises a flat member including multiple sizer portions, each of the multiple sizer portions including a circular depression having a diameter corresponding to a specific diameter of the head. In another exemplary embodiment, the diameter is displayed by way of a size indicator within the circular depression. In another exemplary embodiment, the head sizer and assembly tray is configured to facilitate assembling the one or more implants to be implanted.

In another exemplary embodiment, the impactor is a generally cylindrical member having a concentric hole and a flat surface disposed at each of opposite ends of the impactor. In another exemplary embodiment, the concentric hole is configured to receive a portion of a stem comprising the one or more implants; and wherein the flat surface is configured to be struck with a mallet to push the stem into a head comprising the one or more implants. In another exemplary embodiment, the concentric hole at one end of the impactor has a first depth suitable for receiving a standard size stem and the concentric hole at the opposite end of the impactor has a second depth suitable for receiving a longer size stem.

In an exemplary embodiment, a method for a radial head fracture treatment system comprises: configuring one or more implants for radial head arthroplasty; configuring a head sizer and assembly tray to correspond to sizes of the one or more implants; and assembling a sterile instrument kit comprising a multiplicity of instruments including any one or more of trial heads and trial stems, a starter awl, a reamer, a planar, an inserter cap, and an impactor, the multiplicity of instruments being configured for implanting the one or more implants into a patient's body such that the implant restores biomechanical properties of the native radial head.

In another exemplary embodiment, assembling the sterile instrument kit includes manufacturing any one or more of the starter awl, the reamer, and the planar by injection molding a proximal handle comprising a biocompatible plastic onto a shaft to form an instrument for performing the radial head arthroplasty. In another exemplary embodiment, assembling further comprises: storing the one or more implants in a first sterile container; storing any one or more of the multiplicity of instruments in a second sterile container; and storing the head sizer and assembly tray in a third sterile container.

These and other features of the concepts provided herein may be better understood with reference to the drawings, description, and appended claims.

BRIEF DESCRIPTION OF THE DRAWINGS

The drawings refer to embodiments of the present disclosure in which.

Figure 1:
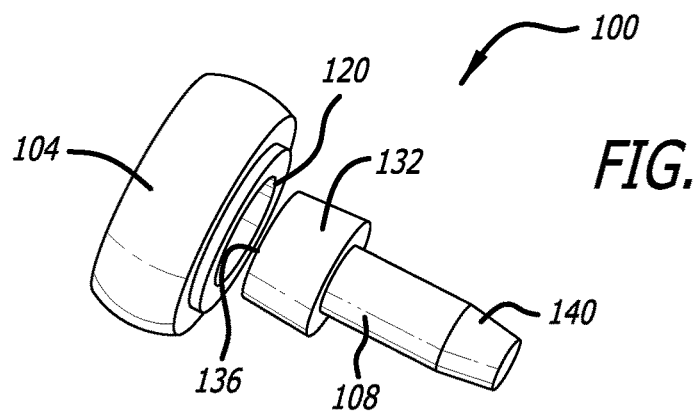
FIG. 1 illustrates an exploded isometric view of an exemplary embodiment of an implant that is suitable for radial head arthroplasty, according to the present disclosure.

While the present disclosure is subject to various modifications and alternative forms, specific embodiments thereof have been shown by way of example in the drawings and will herein be described in detail. The invention should be understood to not be limited to the particular forms disclosed, but on the contrary, the intention is to cover all modifications, equivalents, and alternatives falling within the spirit and scope of the present disclosure.

DETAILED DESCRIPTION

In the following description, numerous specific details are set forth in order to provide a thorough understanding of the present disclosure. It will be apparent, however, to one of ordinary skill in the art that the invention disclosed herein may be practiced without these specific details. In other instances, specific numeric references such as "first implant," may be made. However, the specific numeric reference should not be interpreted as a literal sequential order but rather interpreted that the "first implant" is different than a "second implant." Thus, the specific details set forth are merely exemplary. The specific details may be varied from and still be contemplated to be within the spirit and scope of the present disclosure. The term "coupled" is defined as meaning connected either directly to the component or indirectly to the component through another component. Further, as used herein, the terms "about," "approximately," or "substantially" for any numerical values or ranges indicate a suitable dimensional tolerance that allows the part or collection of components to function for its intended purpose as described herein.

Radial head fractures that are displaced but are too comminuted to be anatomically reduced and stably fixed with ORIF and are too large for fragment excision should be managed by radial head excision or arthroplasty. Patients known to have or likely to have an associated ligamentous injury of the elbow or forearm should undergo a radial head arthroplasty because radial head excision is contraindicated.

Embodiments presented herein provide a system and methods for treating radial head fractures to restore the biomechanical properties of the native radial head when radial head arthroplasty is indicated.

Figure 2:
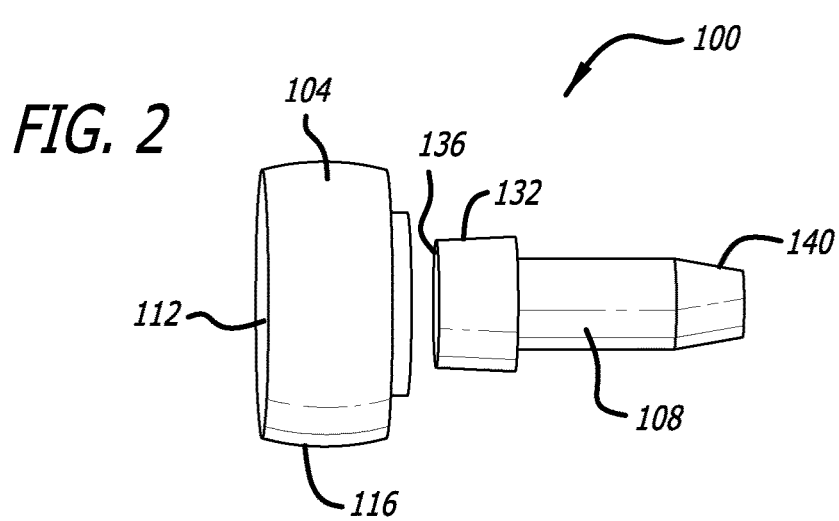
FIG. 2 illustrates an exploded side view of an exemplary embodiment of an implant that is suitable for radial head arthroplasty.

FIGS. 1-2 illustrate an exemplary embodiment of an implant 100 that is suitable for radial head arthroplasty, according to the present disclosure. The implant 100 is generally smooth and comprises a rigid biocompatible material, such as cobalt-chromium (CoCr) or other similar material. The implant 100 includes a head 104 that is coupled with a stem 108. The head 104 is a generally cylindrical member that includes a contact surface 112, a rounded periphery 116, and a tapered bore 120. The rounded periphery 116 comprises a smooth surface that is configured to contact bone and tissues surrounding a radiocapitellar joint 124 (see FIG. 3) without causing damage or trauma to the bone and tissues. The contact surface 112 is adapted to be placed into contact with a capitellum 128 comprising the joint 124. As shown in FIG. 2, the contact surface 112 includes a concavity configured to be placed into sliding contact with the capitellum 128. The concavity of the contact surface 112 facilitates articulation with the capitellum 128, such that the implant 100 restores the biomechanical properties of the native radial head.

As best shown in FIG. 1, the tapered bore 120 is substantially concentric with the head 104 and configured to receive a tapered shank 132 comprising the stem 108. In some embodiments, the tapered shank 132 comprises a Morse taper that enables the stem 108 to be fixedly inserted into the tapered bore 120. As such, the head 104 and the stem 108 may be assembled by inserting the tapered shank 132 into the taper bore 120, placing an impactor onto the stem 108, and then firmly striking the impactor with a mallet, as described herein. It is contemplated that the tapered shank 132 is not to be limited to the Morse taper, however, but rather the tapered shank 132 may comprise any shape or mechanism, such as any of various other tapers, suitable for fixating the shank 132 within the bore 120, without limitation.

The stem 108 is an elongate member extending from a truncated end 136 of the tapered shank 132 to a tapered tip 140. In general, the stem 108 is configured to be inserted into a hole reamed into a medullary canal, as described herein. The tapered tip 140 includes smooth edges that are configured to facilitate inserting the stem 108 into the hole. The stem 108 is relatively short so as to provide stability to the implant 100 while also avoiding extending too deeply into the medullary canal. The tapered shank 132 is configured to be fixated within the tapered bore 120, as described above, so as to keep the head 104 mounted onto a radial neck, as described herein.

Figure 3:
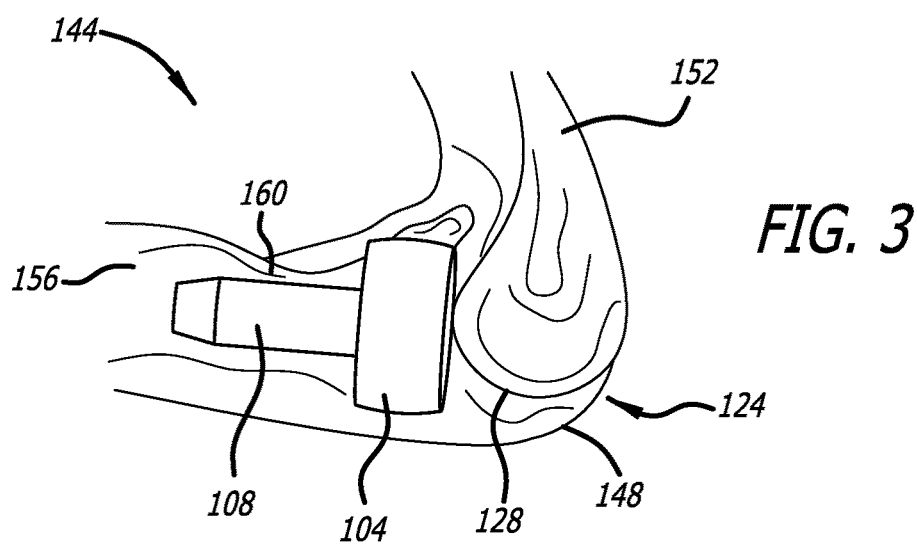
FIG. 3 illustrates an exemplary-use environment wherein the implant of FIGS. 1-2 is implanted into a radiocapitellar joint of a patient.

FIG. 3 illustrates an exemplary-use environment 144 wherein the implant 100 has been implanted into a radiocapitellar joint 124 by way of radial head arthroplasty to treat a radial neck fracture and restore biomechanical properties of the joint 124. In the exemplary-use environment 144 of FIG. 3, the implant 100 is positioned adjacent to the ulna 148 and enables articulation between the humerus 152 and the radius 156. The contact surface 112 of the head 104 facilitates smooth articulation with the capitellum 128. The radial head and any bone fragments have been resected and removed, and the stem 108 has been inserted into the radial neck 160 so as to mount the head 104 onto the radius 156. As described above, a hole is to be reamed into the medullary canal to facilitate inserting the stem 108 into the radius 156. It is contemplated that the resection should be perpendicular and at the level of the radial neck fracture.

Figure 4:
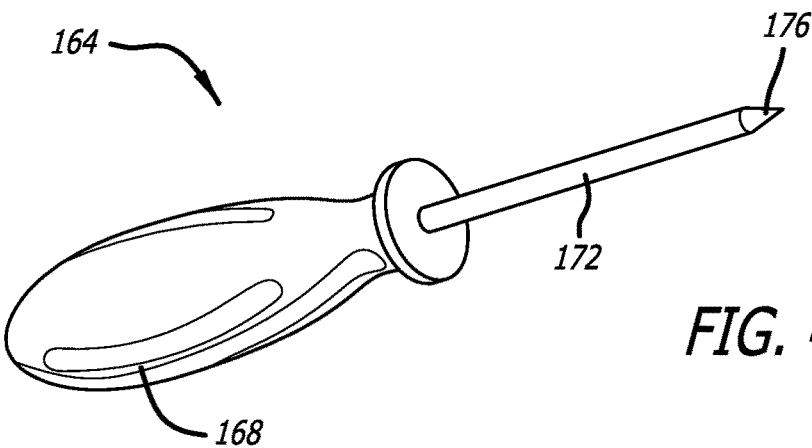
FIG. 4 illustrates an isometric view of an exemplary embodiment of a starter awl for creating an opening in a radial head medullary canal during a radial head arthroplasty.

FIGS. 4 through 9 illustrate exemplary embodiments of instruments that may advantageously be used to perform radial head arthroplasty so as to treat a radial neck fracture, as discussed with reference to FIG. 3. FIG. 4 illustrates an exemplary embodiment of a starter awl 164 that is configured for creating an opening in the medullary canal during a radial head arthroplasty. The starter awl 164 is a generally elongate member comprising a proximal handle 168 coupled with a shaft 172 that terminates at a distal tip 176. The shaft 172 comprises a metal or other rigid material suitable for being pressed against the medulla of the radius 156. The distal tip 176 is advantageously pointed to enable a surgeon to form an opening in the medulla by pressing the distal tip 176 into the medulla. The proximal handle 168 is configured to be grasped in a hand during pressing the distal tip 176 into the medulla. It is contemplated that the proximal handle 168 may comprise any of various suitable biocompatible plastics that may be injection molded onto the shaft 172 during manufacturing the starter awl 164.

Figure 5:
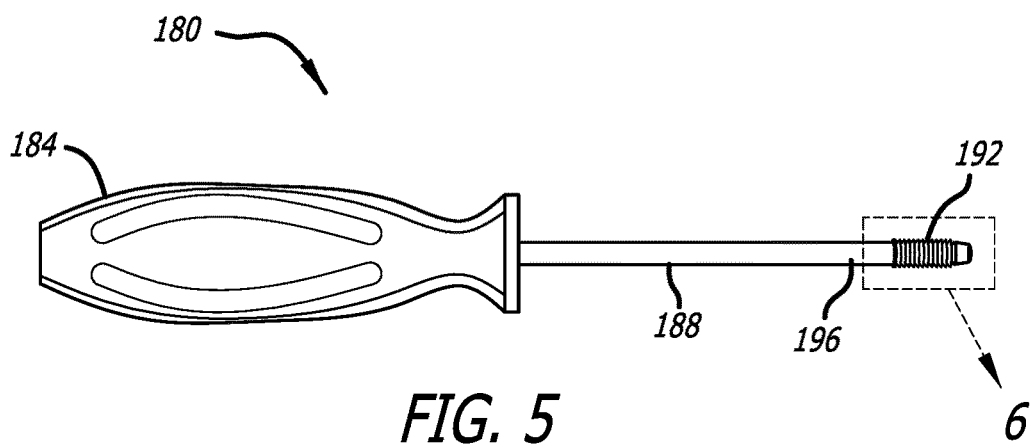
FIG. 5 illustrates a side view of an exemplary embodiment of a reamer for forming a hole in the radial head medullary canal during the radial head arthroplasty.

FIG. 5 illustrates an exemplary embodiment of a reamer 180 that is configured to be used to form a hole in the medullary canal to receive the implant 100 during a radial head arthroplasty. The reamer 180 is an elongate member comprising a proximal handle 184 coupled with a shaft 188 that terminates at a distal cutting teeth area 192. The shaft 188 is substantially similar to the shaft 172, shown in FIG. 4, and thus the shaft 188 comprises a metal or other rigid material capable of reaming a hole into the medullary canal of the radius 156, shown in FIG. 3. The proximal handle 184 is substantially similar to the handle 168 of FIG. 4. As such, the proximal handle 184 is configured to be grasped in a hand during reaming a medullary hole. Like the handle 168, the proximal handle 184 may comprise any of various suitable biocompatible plastics that may be injection molded onto the shaft 188 during manufacturing the reamer 180.

Figure 6:
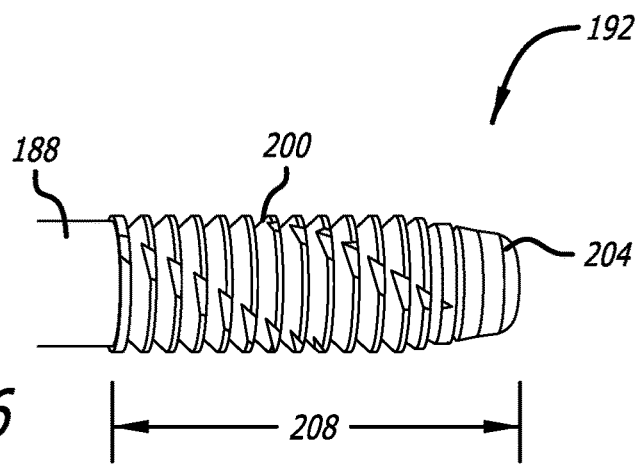
FIG. 6 illustrates a close-up view of an exemplary embodiment of circumferential teeth comprising the reamer of FIG. 5.

The shaft 188 shown in FIG. 5 is substantially similar to the shaft 172, shown in FIG. 4, with the exception that the shaft 188 includes the distal cutting teeth area 192 and a depth indicator 196. As best shown in FIG. 6, the distal cutting teeth area 192 includes circumferential cutting teeth 200 that terminate at a tapered tip 204. The circumferential cutting teeth 200 include a helical crosscut and are configured to form a hole in the medulla when a surgeon uses the proximal handle 184 to twist the reamer 180 in a clockwise direction. The tapered tip 204 is adapted to guide the shaft 188 into the medulla during cutting the hole. In some embodiments, the tapered tip 204 may be configured to form a taper at a bottom of the reamed hole that is similar to the shape of the tapered tip 140 of the implant 100.

As shown in FIG. 6, the circumferential cutting teeth 200 are disposed along a length 208 of the shaft 188. It is contemplated that the length 208 serves to provide a surgeon with a visual indication of the depth to which the shaft 188 is extending into the medullary canal during reaming. As such, the length 208 can provide the surgeon with a depth gauge corresponding to the length of the stem 108 comprising the implant 100 shown in FIGS. 1-2. In the embodiment illustrated in FIG. 6, the length 208 is configured to correspond to the length of a relatively short stem 108 comprising the implant 100. The depth required by longer stems 108 may be indicated by the depth indicator 196. In the illustrated embodiment of FIG. 5, the depth indicator 196 comprises one or more laser markings disposed along the shaft 188. It is contemplated that during twisting the reamer 180 to form a hole in the medulla, the hole has a desirable depth once the depth indicator 196, or the length 208, aligns with the visible surface of the medulla.

Figure 7:
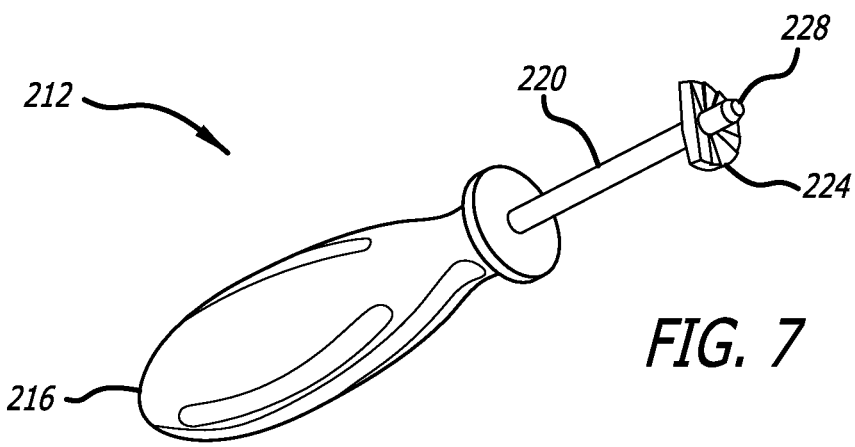
FIG. 7 illustrates an isometric view of an exemplary embodiment of a planar for forming a smooth contact surface on a radial neck during the radial head arthroplasty.

FIG. 7 illustrates an exemplary embodiment of a planar 212 configured to enable a surgeon to form a smooth contact surface on a radial neck 160 during a radial head arthroplasty. As will be appreciated, the contact surface facilitates supporting the head 104 on the radial neck 160, as shown in FIG. 3. The planar 212 shown in FIG. 7 comprises an elongate member that includes a proximal handle 216 coupled with a shaft 220 that includes planar cutting teeth 224 and a distal stem 228. The shaft 220 comprises a metal or other rigid material suitable for cutting the smooth surface into the radial neck 160. The planar cutting teeth 224 are configured for cutting the smooth surface perpendicular to the shaft 220 when the surgeon twists the proximal handle 216 in a clockwise direction. The distal stem 228 is configured to ride inside the hole reamed into the medulla during cutting the smooth surface. As will be appreciated, inserting the distal stem 228 into the medullary hole provides a pivot that advantageously stabilizes the planar cutting teeth 224 during cutting the radial neck 160. The proximal handle 216 is configured to be grasped in a hand during inserting the distal stem 228 into the medullary hole and during twisting the planar 212 to cut the smooth contact surface into the radial neck 160. It is contemplated that the proximal handle 216 may comprise any of various suitable biocompatible plastics that may be injection molded onto the shaft 220 during manufacturing the planar 212.

Figure 8:
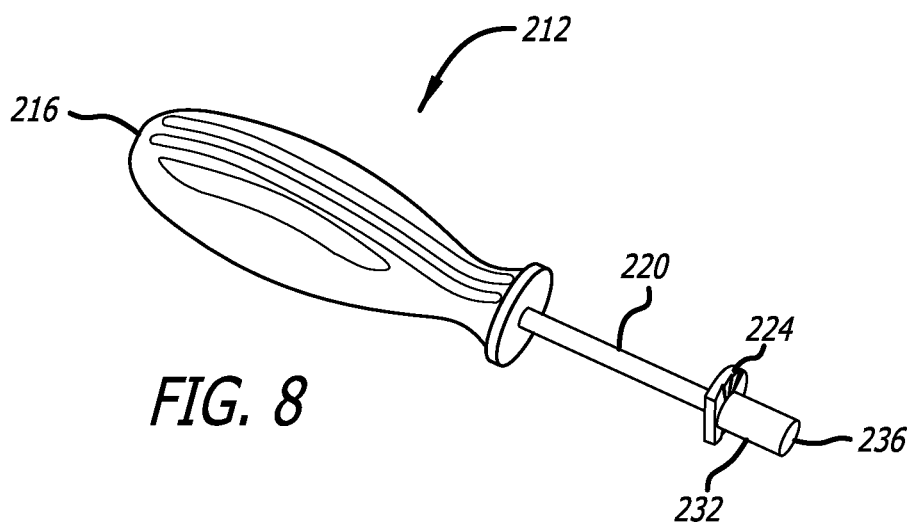
FIG. 8 illustrates an isometric view of the planar of FIG. 7 coupled with an exemplary embodiment of an inserter cap for pushing the implant of FIGS. 1-2 into the hole in the radial head medullary canal during the radial head arthroplasty.

It is contemplated that, in some embodiments, the planar cutting teeth 224 and the distal stem 228 of the planar 212 may advantageously enable a surgeon to press the implant 100 into the medullary hole. For example, FIG. 8 illustrates an exemplary embodiment of an inserter cap 232 coupled with the planar 212 of FIG. 7 and configured for pushing the implant 100 of FIGS. 1-2 into the hole in the radial head medullary canal during a radial head arthroplasty. The inserter cap 232 generally comprises a central hole (not shown) and a smooth distal surface 236. The central hole is adapted to receive the distal stem 228 such that the inserter cap 232 is removably fixated onto the planar 212 as shown in FIG. 8.

Figure 9:
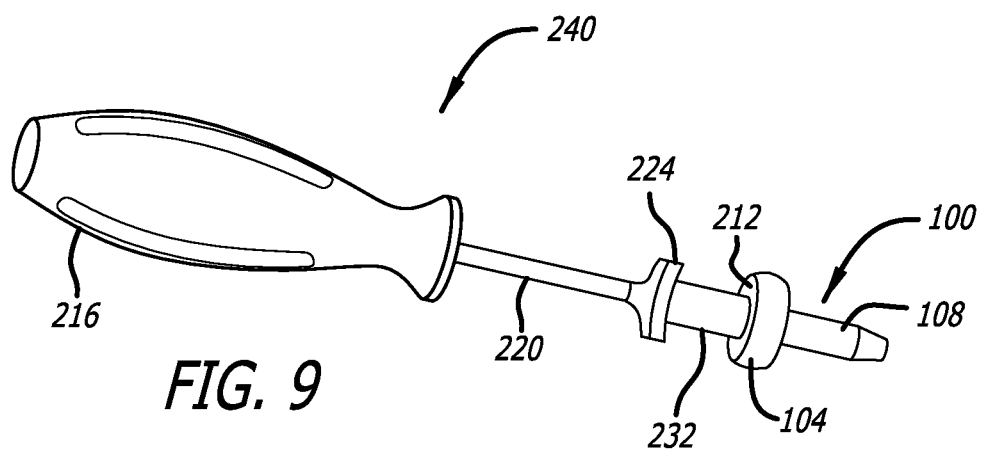
FIG. 9 illustrates an exemplary-use environment wherein the planar and inserter cap of FIG. 8 are being used to push on the implant of FIGS. 1-2.

The distal surface 236 is configured to be pressed against the contact surface 112 of the head 104 during pushing the implant 100 into the medullary hole. For example, FIG. 9 illustrates an exemplary-use environment 240 wherein the planar 212 and inserter cap 232 of FIG. 8 are being used to push the implant 100 of FIGS. 1-2. As shown in FIG. 9, the inserter cap 232 is mounted onto the distal stem 228 of the planar 212 and distal surface 236 is placed into contact with the contact surface 112 of the implant 100 such that the stem 108 is longitudinally aligned with the shaft 220. In the exemplary-use environment 240 of FIG. 9, the surgeon can grasp the proximal handle 216 and push the inserter cap 232 against the head 104 to insert the stem 108 into the medullary hole.

Figure 10:
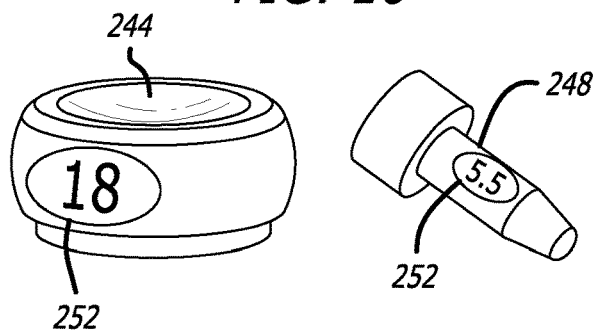
FIG. 10 illustrates an exemplary embodiment of a trial head and a trial stem for determining a suitable size of the implant of FIGS. 1-2 to be implanted into a patient during the radial head arthroplasty.

As will be recognized, determining a suitable size of the implant 100 to be implanted into the radiocapitellar joint 124, shown in FIG. 3, is a crucial part of performing a radial head arthroplasty. To this end, FIG. 10 illustrates an exemplary embodiment of a trial head 244 and a trial stem 248 for advantageously determining a suitable size of the implant 100 during the radial head arthroplasty. The trial head 244 and the trial stem 248 are respectively similar to the head 104 and the stem 108, with the exception that the trial head 244 and the trial stem 248 are configured for size determinations and are not intended for long term implantation in the patient. As such, the trial head 244 and the trial stem 248 each includes a size indication 252. The size indication 252 advantageously enables a surgeon to select an optimal size of the head 104 and the stem 108.

During the radial head arthroplasty, the trial head 244 and the trial stem 248 may be assembled and temporarily placed into the joint 124 (see FIG. 3). As will be appreciated, the joint 124 is reduced and sizing may be assessed through a full range of motion. It is contemplated that before deciding on a final implant size combination, the surgeon may confirm the size and spacing of the trial head 244 and the trial stem 248 by using fluoroscopy. Further, the lateral and medial sides of the humeroulnar joint space should be symmetric. Once an optimal size combination of the trial head 244 and the trial stem 248 are determined, the size indications 252 may be used to identify the sizes of the head 104 and stem 108 to permanently implant into the joint 124.

With continuing reference to FIG. 10, it is contemplated that the trial head 244 and the trial stem 248, as well as the corresponding head 104 and stem 108, may be implemented in a wide variety of suitable sizes, with limitation. For example, in some embodiments, the stems 108, 248 may be provided in a standard size and a longer size. In some embodiments, the longer size is about 8 mm longer than the standard size and adapted for applications requiring additional stability. Similarly, the heads 104, 244 may be implemented with various sizes in diameter and height, without limitation. For example, in some instances it may be necessary to adjust only the height of the trial head 244 to facilitate a proper joint 124 spacing. Thus, in some embodiments, the heads 104, 244 may be provided in various "plus-height" sizes, without limitation. In some embodiments, the plus-height sizes may range between about +2 millimeters (mm) and about +4 mm greater than a standard height of the heads 104, 244.

Figure 11:
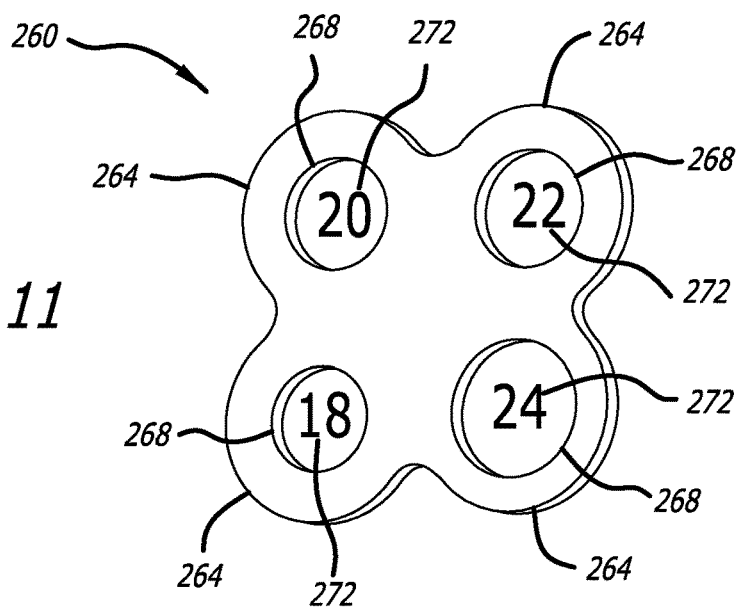
FIG. 11 illustrates an isometric view of an exemplary embodiment of a head sizer and assembly tray for sizing and assembling a head and a stem comprising the implant of FIGS. 1-2.

FIG. 11 illustrates an exemplary embodiment of a head sizer and assembly tray 260 (hereinafter, "tray") configured to enable a surgeon to determine a suitable diameter of the head 104 of the implant 100 to be implanted during the radial head arthroplasty. The tray 260 is a generally flat member comprising multiple sizer portions 264. In the embodiment of FIG. 11, the tray 260 includes four sizer portions 264, however any number of sizer portions 264 may be incorporated into the tray 260, without limitation. Each sizer portion 264 includes a circular depression 268 having a diameter corresponding to specific diameter of the head 104 (see FIG. 1) and the corresponding trial head 244. The diameter of the circular depression 268 is displayed by way of a size indicator 272 within the depression 268.

It is contemplated that a surgeon may use the depressions 268 to determine a size of the trial head 244 to implant into the joint 124 (see FIG. 3). For example, the surgeon may gather radial head fragments that are resected from the joint 124 and then place them into the depressions 268 to identify a best fit that most closely matches the diameter of the native radial head. Once a depression 268 comprising the best fit is found, the surgeon may select a trial head 244 having a diameter specified by the size indicator 272 within the depression 268.

Figure 12:
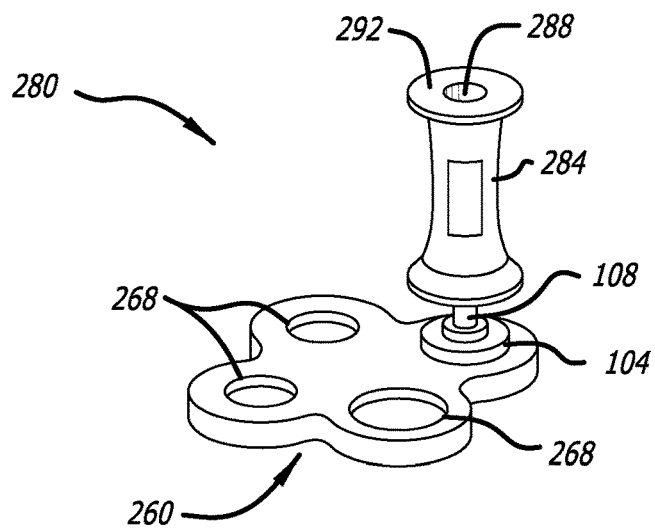
FIG. 12 illustrates an exemplary-use environment wherein an exemplary embodiment of an impactor and the tray of FIG. 11 are being used to assemble the implant of FIGS. 1-2 in accordance with the present disclosure.

In addition to enabling the surgeon to determine the diameter of the trial head 244, the tray 260 is further configured to enable the surgeon to assembly the implant 100 to be implanted into the joint 124. FIG. 12 illustrates an exemplary-use environment 280 wherein an exemplary embodiment of an impactor 284 and the tray 260 of FIG. 11 are being used to assemble the head 104 and the stem 108 of FIGS. 1-2. The impactor 284 is a generally cylindrical member having a concentric hole 288 and a flat surface 292 disposed at each of opposite ends of the impactor 284. The holes 288 are configured to receive a portion of the stem 108 such that striking the flat surface 292 with a mallet pushes the stem 108 into the head 104. In some embodiments, the holes 288 disposed at opposite ends of the impactor 284 may have different depths, corresponding to different lengths of the stem 108. For example, the hole 288 at one end of the impactor 284 may have a depth suitable for receiving a standard size stem 108 while the hole 288 at the opposite end of the impactor 284 may have a depth suitable for receiving a longer size stem 108.

As shown in the exemplary-use environment 280 of FIG. 12, the head 104 may be placed into a depression 268 having a diameter that corresponds to the diameter of the head 104. The contact surface 112 of the head 104 generally is oriented downward into the depression 268 and the tapered bore 120 is faced upward to receive the tapered shank 132 of the stem 108, as described in connection with FIGS. 1-2. The impactor 284 may be placed onto the stem 108 and then the flat surface 292 may be struck with a mallet to fixate the tapered shank 132 of the stem 108 in the tapered bore 120 of the head 104, as described above.

Once the stem 108 and the head 104 are assembled, the implant 100 may be inserted into a medullary hole that has been reamed into a medullary canal of a radial neck 160 (see FIG. 3). The implant 100 may be inserted into the medullary hole either by way of finger control or by way of the planar 212 and the inserter cap 232, as discussed with respect to FIG. 9. After the implant 100 is desirably implanted, the elbow of the patient may be manipulated through its full range of motion to confirm optimal alignment of the implant 100. In some instances, the surgeon may use fluoroscopy to provide additional confirmation of proper alignment of the implant 100 before repairing soft tissues surrounding the joint 124 and closing the incision.

It is envisioned that any one more of the instruments disclosed hereinabove, as well as various size combinations of the implant 100, may be suitably sterilized for surgeries and packaged into sterilized containers. For example, in some embodiments, a sterile instrument kit for treating a fractured radial head comprises one or more implants 100, corresponding trial heads 244 and trial stems 248, a starter awl 164, a reamer 180, a planar 212, an inserter cap 232, a tray 260, and an impactor 284. In some embodiments, the tray 260 is packaged in a first sterile container, while the starter awl 164, the reamer 180, the planar 212, the inserter cap 232, and the impactor 284 are packaged in a second sterile container, and the implants 100 and trials are packed in a third sterile container. The first, second, and third sterile containers are then bundled together into a single, exterior container, thereby forming a convenient surgery-specific radial head fracture treatment package. It is envisioned that other packaging techniques will be apparent to those skilled in the art without deviating from the spirit and scope of the present disclosure.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. To the extent there are variations of the invention, which are within the spirit of the disclosure or equivalent to the inventions found in the claims, it is the intent that this patent will cover those variations as well. Therefore, the present disclosure is to be understood as not limited by the specific embodiments described herein, but only by scope of the appended claims.

What is claimed is:

1. A system for treating radial head fractures, the system comprising:
   one or more implants configured for radial head arthroplasty;
   one or more sterile instrument kits comprising a multiplicity of instruments including any one or more of trial heads and trial stems, a starter awl, a reamer, a planar, an inserter cap, and an impactor, the multiplicity of instruments being configured for implanting the one or more implants into a patient's body such that the implant restores biomechanical properties of the native radial head;
   a head sizer and assembly tray configured to correspond to sizes of the one or more implants;
   wherein the inserter cap is configured to be coupled with the planar for pushing any one of the one or more implants into a radial head medullary hole during a radial head arthroplasty;
   wherein the inserter cap comprises a central hole and a smooth distal surface, the central hole adapted to receive a distal stem extending from the planar wherein the inserter cap is removably fixated onto the planar; and
   wherein the distal surface is configured to be pressed against the any one of the one or more implants.

2. The system of claim 1, wherein the one or more implants each includes a head that is coupled with a stem.

3. The system of claim 2, wherein the head is a cylindrical member comprising:
   a rounded periphery comprising a smooth surface configured to contact bone and tissues surrounding a radiocapitellar joint without causing damage or trauma to the bone and tissues;
   a contact surface adapted to be placed into sliding contact with a capitellum comprising the radiocapitellar joint; and
   a tapered bore configured to fixedly receive a tapered shank comprising the stem.

4. The system of claim 2, wherein the stem is an elongate member configured to be inserted into a hole reamed into a medullary canal of a radial head and comprises:
   a tapered shank configured to be fixated within a tapered bore of the head; and
   a tapered tip configured to facilitate inserting the stem into the hole.

5. The system of claim 1, wherein the starter awl comprises a proximal handle coupled with a shaft that terminates at a distal tip and is configured for creating an opening in a radial head medullary canal during a radial head arthroplasty.

6. The system of claim 5, wherein the proximal handle comprises a biocompatible plastic that is injection molded onto the shaft during manufacturing the starter awl.

7. The system of claim 1, wherein the reamer comprises a proximal handle coupled with a shaft that terminates at a distal cutting teeth area and is configured to be used to form a hole in a radial head medullary canal during a radial head arthroplasty.

8. The system of claim 7, wherein the proximal handle comprises a biocompatible plastic that is injection molded onto the shaft during manufacturing the reamer.

9. The system of claim 1, wherein the planar comprises a proximal handle coupled with a shaft that includes planar cutting teeth and a distal stem, the planar being configured to facilitate forming a smooth contact surface on a radial neck during a radial head arthroplasty.

10. The system of claim 9, wherein the proximal handle is configured to be grasped in a hand during inserting the distal stem into a radial head medullary hole and during twisting the planar to cut the smooth contact surface into the radial neck.

11. The system of claim 9, wherein the proximal handle comprises a biocompatible plastic that is injection molded onto the shaft during manufacturing the planar.

12. The system of claim 1, wherein the head sizer and assembly tray is configured to facilitate determining a suitable diameter of a head comprising the one or more implants to be implanted during a radial head arthroplasty.

13. The system of claim 12, wherein the tray comprises a flat member including multiple sizer portions, each of the multiple sizer portions including a circular depression having a diameter corresponding to a specific diameter of the head.

14. The system of claim 13, wherein the diameter is displayed by way of a size indicator within the circular depression.

15. The system of claim 13, wherein the head sizer and assembly tray is configured to facilitate assembling the one or more implants to be implanted.

16. The system of claim 1, wherein the impactor is a generally cylindrical member having a concentric hole and a flat surface disposed at each of opposite ends of the impactor.

17. The system of claim 16, wherein the concentric hole is configured to receive a portion of a stem comprising the one or more implants; and wherein the flat surface is configured to be struck with a mallet to push the stem into a head comprising the one or more implants.

18. The system of claim 17, wherein the concentric hole at one end of the impactor has a first depth suitable for receiving a standard size stem and the concentric hole at the opposite end of the impactor has a second depth suitable for receiving a longer size stem.

19. A method for a radial head fracture treatment system, the method comprising:
    configuring one or more implants for radial head arthroplasty;
    configuring a head sizer and assembly tray to correspond to sizes of the one or more implants; and
    assembling a sterile instrument kit comprising a multiplicity of instruments including any one or more of trial heads and trial stems, a starter awl, a reamer, a planar, an inserter cap, and an impactor, the multiplicity of instruments being configured for implanting the one or more implants into a patient's body such that the implant restores biomechanical properties of the native radial head;
    coupling the inserter cap with the planar for pushing any one of the one or more implants into a radial head medullary hole during a radial head arthroplasty;
    providing the inserter cap with a central hole and a smooth distal surface, the central hole adapted to receive a distal stem extending from the planar wherein the inserter cap is removably fixated onto the planar; and
    configuring the distal surface to be pressed against the any one of the one or more implants.

20. The method of claim 19, wherein assembling the sterile instrument kit includes manufacturing any one or more of the starter awl, the reamer, and the planar by injection molding a proximal handle comprising a biocompatible plastic onto a shaft to form an instrument for performing the radial head arthroplasty.

21. The method of claim 20, wherein assembling further comprises:
    storing the one or more implants in a first sterile container;
    storing any one or more of the multiplicity of instruments in a second sterile container; and
    storing the head sizer and assembly tray in a third sterile container.

* * * * *